US012751817B2

(12) United States Patent
Orlov et al.

(10) Patent No.: US 12,751,817 B2
(45) Date of Patent: Oct. 6, 2026

(54) VALVE FRAME FOR PROSTHETIC TRICUSPID VALVE

(71) Applicant: SHEBA IMPACT LTD., Ramat-Gan (IL)

(72) Inventors: Boris Orlov, Rishon (IL); Ehud Raanani, Hod (IL)

(73) Assignee: SHEBA IMPACT LTD., Ramat-Gan (IL)

( * ) Notice: Subject to any disclaimer, the term of this patent is extended or adjusted under 35 U.S.C. 154(b) by 880 days.

(21) Appl. No.: 17/906,332

(22) PCT Filed: Jun. 16, 2022

(86) PCT No.: PCT/IB2022/055593
§ 371 (c)(1),
(2) Date: Sep. 14, 2022

(87) PCT Pub. No.: WO2022/264082
PCT Pub. Date: Dec. 22, 2022

(65) Prior Publication Data

US 2024/0207045 A1 Jun. 27, 2024

Related U.S. Application Data

(60) Provisional application No. 63/211,602, filed on Jun. 17, 2021.

(51) Int. Cl.
*A61F 2/24* (2006.01)

(52) U.S. Cl.
CPC .......... *A61F 2/2418* (2013.01); *A61F 2/2436* (2013.01); *A61F 2220/0008* (2013.01); *A61F 2230/005* (2013.01); *A61F 2250/001* (2013.01)

(58) Field of Classification Search
CPC .................. A61F 2/2418; A61F 2/2436; A61F 2220/0008; A61F 2230/005; A61F 2250/001
See application file for complete search history.

(56) References Cited

U.S. PATENT DOCUMENTS 6,270,520 B1 8/2001 Inoue
7,018,408 B2 3/2006 Bailey et al.
(Continued)

FOREIGN PATENT DOCUMENTS

AU 2014202116 A1 5/2014
CA 2606101 A1 11/2006
(Continued)

OTHER PUBLICATIONS

Examination Report for Indian Application No. 20217021772 mailed Jan. 11, 2023.
(Continued)

*Primary Examiner* — Suzette J Gherbi
(74) *Attorney, Agent, or Firm* — Ballard Spahr LLP

(57) ABSTRACT

Apparatus and methods are described for use with a native tricuspid valve of a heart of a mammalian subject. A valve frame (22) includes a valve-frame body (32) that is configured to support prosthetic valve leaflets (20) within the native tricuspid valve. Chord-recruiting arms (30) are configured to extend from the valve-frame body at circumferential regions corresponding to the anterior leaflet and the posterior leaflet of the native tricuspid valve. An anchoring arm (28) is configured to extend from the valve-frame body at a circumferential region corresponding to the septal leaflet of the native tricuspid valve, the anchoring arm (28) being longer than each of the chord-recruiting arms (30). Other applications are also described.

21 Claims, 8 Drawing Sheets

(56) References Cited

U.S. PATENT DOCUMENTS

| | | | | |
|---|---|---|---|---|
| 7,621,948 | B2 | 11/2009 | Herrmann et al. | |
| 7,748,389 | B2 | 7/2010 | Salahieh et al. | |
| 7,753,949 | B2 | 7/2010 | Lamphere et al. | |
| 8,070,802 | B2 | 12/2011 | Lamphere et al. | |
| 8,870,950 | B2 | 10/2014 | Hacohen | |
| 9,364,326 | B2 | 6/2016 | Yaron | |
| 9,700,412 | B2 | 7/2017 | Yaron et al. | |
| 9,949,830 | B2 | 4/2018 | Solem | |
| 10,105,217 | B2 | 10/2018 | Keränen | |
| 10,130,471 | B2 | 11/2018 | Keränen et al. | |
| 10,238,489 | B2 | 3/2019 | Conklin | |
| 10,292,816 | B2 | 5/2019 | Raanani et al. | |
| 10,292,850 | B2 | 5/2019 | Vad et al. | |
| 10,500,038 | B1 | 12/2019 | Orlov et al. | |
| 11,065,114 | B2 | 7/2021 | Raanani et al. | |
| 11,583,394 | B2 | 2/2023 | Orlov et al. | |
| 11,779,459 | B2 | 10/2023 | Raanani et al. | |
| 12,097,114 | B2 | 9/2024 | Raanani et al. | |
| 2002/0065554 | A1 | 5/2002 | Streeter | |
| 2003/0014104 | A1 | 1/2003 | Cribier | |
| 2003/0083742 | A1 | 5/2003 | Spence et al. | |
| 2004/0138745 | A1 | 7/2004 | Macoviak et al. | |
| 2005/0165479 | A1 | 7/2005 | Drews et al. | |
| 2006/0195134 | A1 | 8/2006 | Crittenden | |
| 2006/0195184 | A1* | 8/2006 | Lane | A61F 2/2418 623/2.38 |
| 2006/0241745 | A1 | 10/2006 | Solem | |
| 2007/0016288 | A1 | 1/2007 | Gurskis et al. | |
| 2007/0050020 | A1 | 3/2007 | Spence | |
| 2007/0260305 | A1 | 11/2007 | Drews et al. | |
| 2007/0293942 | A1 | 12/2007 | Mirzaee | |
| 2008/0039935 | A1 | 2/2008 | Buch et al. | |
| 2009/0192585 | A1 | 7/2009 | Bloom et al. | |
| 2009/0192586 | A1 | 7/2009 | Tabor et al. | |
| 2009/0198324 | A1 | 8/2009 | Orlov | |
| 2009/0281618 | A1 | 11/2009 | Hill et al. | |
| 2010/0022640 | A1 | 1/2010 | Stoutamire | |
| 2010/0030330 | A1* | 2/2010 | Bobo | A61F 2/2442 623/2.38 |
| 2010/0042208 | A1 | 2/2010 | Herrmann et al. | |
| 2010/0049313 | A1 | 2/2010 | Alon et al. | |
| 2010/0082094 | A1 | 4/2010 | Quadri et al. | |
| 2010/0249923 | A1 | 9/2010 | Alkhatib et al. | |
| 2010/0331971 | A1 | 12/2010 | Keraenen et al. | |
| 2011/0029072 | A1 | 2/2011 | Gabbay | |
| 2011/0137397 | A1 | 6/2011 | Chau et al. | |
| 2011/0137410 | A1 | 6/2011 | Hacohen | |
| 2011/0218620 | A1 | 9/2011 | Meiri et al. | |
| 2011/0224785 | A1 | 9/2011 | Hacohen | |
| 2011/0264208 | A1 | 10/2011 | Duffy et al. | |
| 2011/0319989 | A1 | 12/2011 | Lane et al. | |
| 2012/0010461 | A1 | 1/2012 | Goldfarb et al. | |
| 2012/0022633 | A1 | 1/2012 | Olson et al. | |
| 2012/0022639 | A1 | 1/2012 | Hacohen et al. | |
| 2012/0022640 | A1 | 1/2012 | Gross et al. | |
| 2012/0101571 | A1 | 4/2012 | Thambar et al. | |
| 2013/0035759 | A1 | 2/2013 | Gross et al. | |
| 2013/0079873 | A1* | 3/2013 | Migliazza | A61F 2/2412 623/2.17 |
| 2013/0166022 | A1 | 6/2013 | Conklin | |
| 2013/0190861 | A1 | 7/2013 | Chau et al. | |
| 2014/0031928 | A1 | 1/2014 | Murphy et al. | |
| 2014/0088695 | A1 | 3/2014 | Figulla et al. | |
| 2014/0088696 | A1 | 3/2014 | Figulla et al. | |
| 2014/0194975 | A1 | 7/2014 | Quill et al. | |
| 2014/0200662 | A1 | 7/2014 | Eftel et al. | |
| 2014/0222136 | A1 | 8/2014 | Geist et al. | |
| 2014/0222142 | A1 | 8/2014 | Kovalsky et al. | |
| 2014/0324164 | A1 | 10/2014 | Gross et al. | |
| 2014/0379074 | A1 | 12/2014 | Spence et al. | |
| 2015/0045880 | A1 | 2/2015 | Hacohen | |
| 2015/0127093 | A1 | 5/2015 | Hosmer et al. | |
| 2015/0164640 | A1 | 6/2015 | McLean et al. | |
| 2015/0173897 | A1* | 6/2015 | Raanani | A61F 2/2418 623/2.11 |
| 2015/0265400 | A1* | 9/2015 | Eidenschink | A61F 2/2418 623/2.38 |
| 2015/0351903 | A1 | 12/2015 | Morriss et al. | |
| 2015/0351908 | A1 | 12/2015 | Kernen et al. | |
| 2015/0359628 | A1 | 12/2015 | Keränen | |
| 2015/0374493 | A1 | 12/2015 | Yaron et al. | |
| 2016/0045306 | A1 | 2/2016 | Agrawal et al. | |
| 2016/0095705 | A1 | 4/2016 | Keränen et al. | |
| 2016/0310268 | A1 | 10/2016 | Oba et al. | |
| 2017/0128199 | A1 | 5/2017 | Gurovich et al. | |
| 2017/0143478 | A1* | 5/2017 | Schwartz | A61F 2/246 |
| 2017/0216023 | A1* | 8/2017 | Lane | A61F 2/2418 |
| 2017/0266003 | A1 | 9/2017 | Hammer et al. | |
| 2017/0281338 | A1 | 10/2017 | Quill et al. | |
| 2018/0008404 | A1 | 1/2018 | Tamir | |
| 2018/0014932 | A1 | 1/2018 | Hammer et al. | |
| 2018/0125651 | A1 | 5/2018 | Nasr | |
| 2018/0177594 | A1 | 6/2018 | Patel et al. | |
| 2018/0206992 | A1 | 7/2018 | Brown | |
| 2018/0303609 | A1 | 10/2018 | Kenny et al. | |
| 2018/0311037 | A1 | 11/2018 | Morriss et al. | |
| 2018/0318079 | A1 | 11/2018 | Patel et al. | |
| 2019/0083245 | A1 | 3/2019 | Hariton et al. | |
| 2019/0110893 | A1 | 4/2019 | Haarer et al. | |
| 2019/0125534 | A1 | 5/2019 | Arcaro et al. | |
| 2019/0142590 | A1* | 5/2019 | Yeo | A61F 2/2433 623/2.11 |
| 2019/0231520 | A1 | 8/2019 | Desrosiers et al. | |
| 2019/0231522 | A1 | 8/2019 | Raanani et al. | |
| 2020/0100898 | A1 | 4/2020 | Vola et al. | |
| 2020/0121454 | A1 | 4/2020 | Spence | |
| 2020/0138569 | A1* | 5/2020 | Basude | A61F 2/2466 |
| 2020/0179109 | A1* | 6/2020 | Reimer | A61F 2/2418 |
| 2020/0197175 | A1 | 6/2020 | Chang et al. | |
| 2022/0010634 | A1 | 1/2022 | Posa | |
| 2022/0015896 | A1* | 1/2022 | Agian | A61F 2/2466 |
| 2022/0015900 | A1 | 1/2022 | Agian et al. | |
| 2022/0015905 | A1* | 1/2022 | Raanani | A61F 2/2466 |
| 2022/0296370 | A1 | 9/2022 | Agian et al. | |
| 2023/0000622 | A1 | 1/2023 | Raanani et al. | |
| 2023/0172707 | A1 | 6/2023 | Orlov et al. | |
| 2023/0270549 | A1* | 8/2023 | Guidotti | A61F 2/2457 623/2.11 |
| 2023/0372099 | A1* | 11/2023 | Orlov | A61F 2/2418 |
| 2024/0148498 | A1 | 5/2024 | Quadri et al. | |
| 2024/0207045 | A1* | 6/2024 | Orlov | A61F 2/2436 |
| 2025/0268704 | A1* | 8/2025 | Chin | A61F 2/0811 |

FOREIGN PATENT DOCUMENTS

| | | | |
|---|---|---|---|
| CA | 2898991 | A1 | 8/2014 |
| CN | 101180010 | A | 5/2008 |
| CN | 102292053 | A | 12/2011 |
| CN | 102438546 | A | 5/2012 |
| CN | 103517688 | A | 1/2014 |
| CN | 104684505 | A | 6/2015 |
| CN | 104994812 | A | 10/2015 |
| DE | 102006052564 | | 12/2007 |
| EP | 1850796 | B1 | 12/2015 |
| EP | 3315094 | A1 | 5/2018 |
| EP | 3399947 | A1 | 11/2018 |
| EP | 2948102 | B1 | 1/2019 |
| EP | 2852354 | B1 | 5/2020 |
| JP | 2008536592 | A | 9/2008 |
| JP | 2011509806 | A | 3/2011 |
| JP | 2012500665 | A | 1/2012 |
| JP | 2012521222 | A | 9/2012 |
| JP | 2014506175 | A | 3/2014 |
| JP | 2014168694 | A | 9/2014 |
| JP | 2015517376 | A | 6/2015 |
| JP | 2016504134 | A | 2/2016 |
| JP | 2018501001 | A | 1/2018 |
| JP | 2019500965 | A | 1/2019 |
| JP | 7051736 | B2 | 4/2022 |
| WO | 0060995 | A2 | 10/2000 |
| WO | 2004032724 | A2 | 4/2004 |
| WO | 2005087140 | A1 | 9/2005 |
| WO | 2006116558 | A2 | 11/2006 |
| WO | 2007135101 | A1 | 11/2007 |

(56) References Cited

FOREIGN PATENT DOCUMENTS

| | | | | |
|---|---|---|---|---|
| WO | 2009134701 A2 | 11/2009 | | |
| WO | 2010108079 A1 | 9/2010 | | |
| WO | 2012004679 A2 | 1/2012 | | |
| WO | 2012095116 A1 | 7/2012 | | |
| WO | 2013001339 A2 | 1/2013 | | |
| WO | WO-2013028387 A2 * | 2/2013 | ........... | A61F 2/2418 |
| WO | 2013175468 A2 | 11/2013 | | |
| WO | 2014114795 A1 | 7/2014 | | |
| WO | 2015198125 A1 | 12/2015 | | |
| WO | 2018109329 A1 | 6/2018 | | |
| WO | 2018112429 A1 | 6/2018 | | |
| WO | 2020092096 A2 | 5/2020 | | |
| WO | 2020100050 A1 | 5/2020 | | |
| WO | 2021021368 A1 | 2/2021 | | |
| WO | 2021028867 A1 | 2/2021 | | |
| WO | 2021195090 A1 | 9/2021 | | |
| WO | 2022090881 A1 | 5/2022 | | |
| WO | 2022090882 A1 | 5/2022 | | |
| WO | 2022234468 A1 | 11/2022 | | |
| WO | 2022264082 A1 | 12/2022 | | |
| WO | 2023228028 A1 | 11/2023 | | |
| WO | 2024057226 A1 | 3/2024 | | |

OTHER PUBLICATIONS

Hearing Notice for Indian Application No. 2424/MUMNP/2014 mailed Jan. 3, 2023.
International Search Report and Written Opinion from International Application No. PCT/IB2022/055593 mailed Nov. 14, 2022.
Invitation to Pay Additional Fees for International Application No. PCT/IB2022/055593 mailed Sep. 23, 2022.
U.S. Appl. No. 17/263,776, filed Jan. 27, 2021.
U.S. Appl. No. 17/932,014, filed Sep. 14, 2022.
U.S. Appl. No. 62/767,018, filed Nov. 14, 2018.
U.S. Appl. No. 63/184,403, filed May 5, 2021.
U.S. Appl. No. 63/184,427, filed May 5, 2021.
U.S. Appl. No. 63/211,602, filed Jun. 17, 2021.
Advisory Action for U.S. Appl. No. 14/402,387 mailed Mar. 1, 2018.
Communication Pursuant to Article 94(3) EPC Dated Jan. 8, 2018 From the European Patent Office Re. Application No. 13732633.6.
Communication Pursuant to Rule 94(3) for European Patent Application No. 20760551.0 mailed Apr. 7, 2022.
Communication Relating to the Results of the Partial International Search Dated Nov. 18, 2013 From the International Searching Authority Re. Application No. PCT/IL2013/050432.
Corrected Notice of Allowability for U.S. Appl. No. 14/402,387 mailed Mar. 20, 2019.
Examination Report for Australian Application No. 2013264730 mailed Dec. 20, 2017.
Examination Report for Australian Application No. 2013264730 mailed Jan. 13, 2017.
Examination Report for Australian Application No. 2018202951 mailed Dec. 6, 2018.
Examination Report for Australian Application No. 2019250140 mailed Oct. 19, 2020.
Examination Report for European Application No. 13732633.6 mailed Aug. 8, 2019.
Examination Report for Indian Application No. 2424/MUMNP/2014 mailed Aug. 31, 2020.
Final Office Action for U.S. Appl. No. 14/402,387 mailed Oct. 2, 2017.
Final Office Action for U.S. Appl. No. 13/475,994 mailed Jan. 10, 2017.
Final Office Action for U.S. Appl. No. 13/475,994 mailed Jun. 10, 2015.
International Preliminary Report on Patentability from International Application No. PCT/IL2013/050432 mailed Dec. 4, 2014.
International Search Report and Written Opinion for International Application No. PCT/IB2021/059798 mailed Jan. 24, 2022.
International Search Report and Written Opinion for International Application No. PCT/IB2021/059799 mailed Jan. 25, 2022.
International Search Report and Written Opinion from International Application No. PCT/IB2019/059734 mailed Feb. 6, 2020.
International Search Report and Written Opinion from International Application No. PCT/IB2019/059734 mailed Jan. 30, 2020.
International Search Report and Written Opinion from International Application No. PCT/IB2020/057636 mailed Oct. 29, 2020.
International Search Report and Written Opinion from International Application No. PCT/IL2013/050432 mailed Feb. 26, 2014.
Issue Notification for U.S. Appl. No. 14/402,387 mailed May 1, 2019.
Issue Notification for U.S. Appl. No. 16/374,240 mailed Jun. 30, 2021.
Non-Final Office Action for U.S. Appl. No. 13/475,994 mailed Apr. 1, 2016.
Non-Final Office Action for U.S. Appl. No. 13/475,994 mailed Oct. 1, 2014.
Non-Final Office Action for U.S. Appl. No. 13/475,994 mailed Sep. 11, 2017.
Non-Final Office Action for U.S. Appl. No. 14/402,387 mailed Dec. 23, 2016.
Non-Final Office Action for U.S. Appl. No. 14/402,387 mailed Sep. 20, 2018.
Non-Final Office Action for U.S. Appl. No. 16/655,656 mailed Jun. 17, 2022.
Notice of Allowance for U.S. Appl. No. 14/402,387 mailed Apr. 30, 2019.
Notice of Allowance for U.S. Appl. No. 14/402,387 mailed Jan. 30, 2019.
Notice of Allowance for U.S. Appl. No. 16/374,240 mailed Mar. 16, 2021.
Notice of Amendment Dated Jun. 23, 2017 From the State Intellectual Property Office of the People's Republic of China Re. Application No. 201710425696.6 and Its Machine Translation Into English.
Notice of Reason for Rejection Dated Feb. 14, 2017 From the Japan Patent Office Re. Application No. 2015-513347 and Translation.
Notification of Office Action and Search Report Dated Sep. 7, 2016 From the State Intellectual Property Office of the People's Republic of China Re. Application No. 201380038199.0.
Notification of Office Action Dated Dec. 3, 2015 From the State Intellectual Property Office of the People's Republic of China Re. Application No. 201380038199.0.
Notification of Office Action Dated Dec. 14, 2016 From the State Intellectual Property Office of the People's Republic of China Re. Application No. 201380038199.0 and Its Translation Into English.
Office Action for Australian Application No. 2018202951 mailed Apr. 1, 2019.
Office Action for Canadian Application No. 2,874,208 mailed Aug. 2, 2019.
Office Action for Canadian Application No. 2,874,208 mailed Feb. 19, 2019.
Office Action for Chinese Application No. 20170425696.6 mailed May 19, 2020.
Office Action for Chinese Application No. 201710425696.6 mailed Nov. 4, 2019.
Office Action for Japanese Application No. 2017-184962 mailed Jul. 31, 2018.
Office Action for Japanese Application No. 2019/032726 mailed Feb. 18, 2020.
Office Action for Japanese Application No. 2019/032726 mailed Jan. 19, 2021.
Office Action for Japanese Application No. 2019/032726 mailed Nov. 19, 2021.
Restriction Requirement for U.S. Appl. No. 13/475,994 mailed Mar. 11, 2014.
Translation Dated Dec. 28, 2015 of Notification of Office Action Dated Dec. 3, 2015 From the State Intellectual Property Office of the People's Republic of China Re. Application No. 201380038199.0.

(56) References Cited

OTHER PUBLICATIONS

Translation of Notification of Office Action and Search Report Dated Sep. 7, 2016 From the State Intellectual Property Office of the People's Republic of China Re. Application No. 201380038199.0.
U.S. Appl. No. 12/582,986, filed Oct. 21, 2009.
U.S. Appl. No. 14/402,387, filed Nov. 20, 2014.
U.S. Appl. No. 16/374,240, filed Apr. 3, 2019.
U.S. Appl. No. 17/349,152 filed Jun. 16, 2021.
U.S. Appl. No. 17/488,623, filed Sep. 29, 2021.
U.S. Appl. No. 17/488,628, filed Sep. 29, 2021.
U.S. Appl. No. 61/649,319, filed May 20, 2012.
U.S. Appl. No. 62/886,366, filed Aug. 14, 2019.
Examination Report for European Application No. 21801644.2 mailed May 2, 2024.
Final Office Action for U.S. Appl. No. 17/488,623 mailed May 30, 2024.
International Search Report and Written Opinion from International Application No. PCT/IB2023/059084 mailed Feb. 12, 2024.
Invitation to Pay Additional Fees for International Application No. PCT/IB2023/059084 mailed Dec. 22, 2023.
Non-Final Office Action for U.S. Appl. No. 17/292,987 mailed May 21, 2024.
Non-Final Office Action for U.S. Appl. No. 17/488,628 mailed May 31, 2024.
Non-Final Office Action for U.S. Appl. No. 18/103,671 mailed Apr. 2, 2024.
Notice of Allowance for U.S. Appl. No. 17/263,776 mailed Apr. 9, 2024.
Notice of Allowance for U.S. Appl. No. 17/932,014 mailed May 22, 2024.
Office Action for Chinese Application No. 201980082413 mailed Jan. 31, 2024.
Office Action for Israel Application No. 283093 mailed Feb. 18, 2024.
Office Action for Japanese Application No. 2021-525788 mailed Mar. 11, 2024.
Office Action for Japanese Application No. 2022-508890 mailed Apr. 9, 2024.
Extended European Search Report for European Application No. 23162937.9 mailed Jun. 21, 2023.
International Search Report and Written Opinion from International Application No. PCT/IB2022/054099 mailed Sep. 12, 2022.
Invitation to Pay Additional Fees for International Application No. PCT/IB2022/054099 mailed Jul. 20, 2022.
Notice of Allowance for U.S. Appl. No. 17/349,152 mailed May 24, 2023.
Office Action for Canadian Application No. 3,149,527 mailed Mar. 6, 2023.
U.S. Appl. No. 16/106,000, filed Oct. 27, 2020.
U.S. Appl. No. 16/106,034, filed Oct. 27, 2020.
U.S. Appl. No. 18/248,394, filed Apr. 10, 2023.
U.S. Appl. No. 63/106,000, filed Oct. 27, 2020.
U.S. Appl. No. 63/106,034, filed Oct. 27, 2020.
Applicant-Initiated Interview Summary for U.S. Appl. No. 14/402,387 mailed Dec. 28, 2017.
Applicant-Initiated Interview Summary for U.S. Appl. No. 14/402,387 mailed May 25, 2017.
Final Office Action for U.S. Appl. No. 13/083,643 mailed Mar. 5, 2014.
Final Office Action for U.S. Appl. No. 13/475,994 mailed Jun. 8, 2018.
International Search Report and Written Opinion from International Application No. PCT/IB2023/055160 mailed Jul. 28, 2023.
Issue Notification for U.S. Appl. No. 13/475,994 mailed Nov. 20, 2019.
Issue Notification for U.S. Appl. No. 16/655,656 mailed Feb. 1, 2023.
Issue Notification for U.S. Appl. No. 17/349,152 mailed Sep. 20, 2023.
Non-Final Office Action for U.S. Appl. No. 13/475,994 mailed Dec. 28, 2018.
Non-Final Office Action for U.S. Appl. No. 17/263,776 mailed Oct. 25, 2023.
Non-Final Office Action for U.S. Appl. No. 17/488,623 mailed Oct. 26, 2023.
Non-Final Office Action for U.S. Appl. No. 17/488,628 mailed Oct. 26, 2023.
Notice of Allowance for U.S. Appl. No. 13/475,994 mailed Jul. 22, 2019.
Notice of Allowance for U.S. Appl. No. 16/655,656 mailed Oct. 25, 2022.
Office Action for Japanese Application No. 2021-525788 mailed Nov. 1, 2023.
U.S. Appl. No. 13/475,994, filed May 20, 2012.
U.S. Appl. No. 16/655,656, filed Oct. 17, 2019.
U.S. Appl. No. 18/103,671, filed Jan. 31, 2023.
U.S. Appl. No. 61/488,180, filed May 20, 2011.
Examination Report for Indian Application No. 202247005897 mailed Dec. 11, 2024,.
Final Office Action for U.S. Appl. No. 17/488,628 mailed Jul. 31, 2024,.
Final Office Action for U.S. Appl. No. 18/103,671 mailed Jul. 29, 2024,.
International Search Report and Written Opinion from International Application No. PCT/IB2024/052304 mailed Jun. 17, 2024,.
Issue Notification for U.S. Appl. No. 17/488,628 mailed Oct. 23, 2024,.
Issue Notification for U.S. Appl. No. 17/932,014 mailed Sep. 4, 2024,.
Issue Notification for U.S. Appl. No. 18/103,671 mailed Jan. 8, 2025,.
Non-Final Office Action for U.S. Appl. No. 17/488,623 mailed Jul. 31, 2024,.
Notice of Allowance for U.S. Appl. No. 17/292,987 mailed Mar. 5, 2025,.
Notice of Allowance for U.S. Appl. No. 17/488,623 mailed Jan. 6, 2025,.
Notice of Allowance for U.S. Appl. No. 18/103,671 mailed Sep. 28, 2024,.
Office Action for Chinese Application No. 201980082413.X mailed Sep. 26, 2024,.
Office Action for Israel Application No. 283093 mailed Jan. 16, 2025,.
Office Action for Israel Application No. 290306 mailed Jul. 7, 2024,.
U.S. Appl. No. 18/814,988, filed Aug. 26, 2024,.
U.S. Appl. No. 18/867,696, filed Nov. 20, 2024,.
U.S. Appl. No. 18/994,876, filed Jan. 15, 2025,.
U.S. Appl. No. 18/999,207, filed Dec. 23, 2024,.
U.S. Appl. No. 63/344,590, filed May 22, 2022,.
U.S. Appl. No. 63/405,966, filed Sep. 13, 2022,.
Communication Pursuant to Article 94(3) EPC for European Application No. 21801644.2 mailed Apr. 24, 2025.
Extended European Search Report for European Application No. 22728269.6 mailed Mar. 17, 2025.
Issue Notification for U.S. Appl. No. 17/488,623 mailed Aug. 13, 2025.
Non-Final Office Action for U.S. Appl. No. 17/906,388 mailed Jun. 4, 2025.
Non-Final Office Action for U.S. Appl. No. 18/248,394 mailed Nov. 7, 2025.
Notice of Allowance for U.S. Appl. No. 17/488,623 mailed Apr. 24, 2025.
Notice of Allowance for U.S. Appl. No. 17/906,388 mailed Dec. 9, 2025.
Office Action for Chinese Application No. 202080062891.7 mailed Mar. 5, 2025.
Office Action for Israel Application No. 283093 mailed Jul. 20, 2025.
Restriction Requirement for U.S. Appl. No. 18/248,220 mailed Dec. 5, 2025.
U.S. Appl. No. 17/292,987, filed May 11, 2021 .

(56) References Cited

OTHER PUBLICATIONS

Examination Report for European Application No. 19808898.1 mailed Sep. 10, 2025.
Examination Report for European Application No. 21801644.2 mailed Dec. 19, 2025.
Final Office Action for U.S. Appl. No. 18/248,394 mailed Apr. 21, 2026.
International Search Report and Written Opinion from International Application No. PCT/IB2025/056499 mailed Nov. 28, 2025.
Invitation to Pay Additional Fees for International Application No. PCT/IB2025/056499 mailed Oct. 7, 2025.
Non-Final Office Action for U.S. Appl. No. 18/248,220 mailed Mar. 9, 2026.
Non-Final Office Action for U.S. Appl. No. 18/814,988 mailed Dec. 29, 2025.
Notice Before Refusal for Israel Application No. 283093 mailed Jan. 4, 2026.
Notice of Allowance for U.S. Application No. 17/906, 388 mailed Apr. 14, 2026.
Office Action for Chinese Application No. 202180072657.7 mailed Mar. 13, 2026.
Office Action for Chinese Application No. 202180072661.3 mailed Feb. 9, 2026.
Office Action for Japanese Application No. 2023-566611 mailed Feb. 20, 2026.
Office Action for Japanese Application No. 2024-157831 mailed Nov. 20, 2025.
Office Action for Japanese Application No. 2024-192559 mailed Dec. 8, 2025.
U.S. Appl. No. 19/638,590, filed Apr. 3, 2026.
Office Action for Israel Application No. 308940 issued on Apr. 29, 2026.
Office Action for Japanese Application No. 2023-577560 dated May 1, 2026.

* cited by examiner

VALVE FRAME FOR PROSTHETIC TRICUSPID VALVE

CROSS-REFERENCES TO RELATED APPLICATIONS

The present application is a US national phase application of PCT Application No. PCT/IB2022/055593 to Orlov, filed Jun. 16, 2022, entitled "Valve frame for prosthetic tricuspid valve," which claims priority from U.S. Provisional Patent Application 63/211,602 to Orlov, filed Jun. 17, 2021, entitled "Valve frame for prosthetic tricuspid valve," which is incorporated herein by reference.

FIELD OF EMBODIMENTS OF THE INVENTION

The present invention relates to medical apparatus and methods, and specifically to apparatus and methods for implanting a prosthetic valve at a tricuspid valve.

BACKGROUND

The human heart is a muscular organ that pumps deoxygenated blood through the lungs to oxygenate the blood and pumps oxygenated blood to the rest of the body by contractions of four chambers.

After having circulated in the body, deoxygenated blood from the body enters the right atrium through the vena cava(s). In a healthy subject, the right atrium contracts, pumping the blood through the tricuspid valve into the right ventricle. The right ventricle contracts, pumping the blood through the pulmonary semi-lunar valve into the pulmonary artery which splits to two branches, one for each lung. The blood is oxygenated while passing through the lungs, and reenters the heart via the left atrium. The left atrium contracts, pumping the oxygenated blood through the mitral valve into the left ventricle. The left ventricle contracts, pumping the oxygenated blood through the aortic valve into the aorta to be distributed to the rest of the body. The tricuspid valve closes during right ventricle contraction, so that backflow of blood into the right atrium is prevented. Similarly, the mitral valve closes during left ventricle contraction, so that backflow of blood into the left atrium is prevented. The mitral valve and the tricuspid valve are known as atrioventricular valves, each of these valves controlling the flow of blood between an atrium and a ventricle.

The tricuspid valve includes three leaflets: the septal leaflet, the anterior leaflet, and the posterior leaflet. Each of the valve leaflets is attached to the tricuspid valve annulus, which defines the tricuspid valve orifice. The leaflets are connected to papillary muscles within the right ventricle and/or to the right ventricular wall, by chords. In a healthy subject the tricuspid valve controls the direction of blood flow from the right atrium to the right ventricle, as described above. Tricuspid valve regurgitation occurs when the tricuspid valve fails to close properly. This can cause blood to flow back up into the right atrium when the right ventricle contracts. Tricuspid valve regurgitation is most commonly caused by right ventricle dilation, which leads to the tricuspid valve annulus dilating, resulting in the valve leaflets failing to coapt properly.

SUMMARY OF EMBODIMENTS

In accordance with some applications of the present invention, prosthetic tricuspid valve leaflets are disposed within a prosthetic tricuspid valve frame. The prosthetic tricuspid valve frame is typically delivered to a subject's native tricuspid valve through the subject's inferior or superior vena cava. Typically, the tricuspid valve frame includes an anchoring arm at a circumferential region corresponding to the septal leaflet of the native tricuspid valve and includes a plurality of chord-recruiting arms at circumferential regions corresponding to the anterior and posterior leaflets of the native tricuspid valve. For some applications, the prosthetic tricuspid valve frame includes a valve-frame body that defines a ventricular portion (which upon deployment is configured to be disposed within the subject's right ventricle), and an atrial portion (which upon deployment is configured to be disposed within the subject's right atrium). The prosthetic tricuspid valve frame typically supports a plurality of prosthetic tricuspid valve leaflets (e.g., two leaflets, or three leaflets, as shown), which are sutured or otherwise coupled to the valve-frame body.

Typically, in a non-constrained configuration of the prosthetic tricuspid valve frame, the chord-recruiting arms extend radially from a portion of valve-frame body that is configured to be placed within the subject's ventricle. For some applications, in a non-radially-constrained configuration of the valve frame, the chord-recruiting arms encompass more than 40 percent of the circumference of the valve-frame body (e.g., more than 60 percent of the circumference of the valve-frame body), and/or less than 80 percent of the of the circumference of the valve-frame body (e.g., less than 70 percent of the circumference of the valve-frame body). Typically, the chord-recruiting arms are configured to be disposed at circumferential regions corresponding to the anterior and posterior leaflets of the native tricuspid valve, and are configured to recruit the chords of the aforementioned leaflets, as described in further detail hereinbelow. Typically, the chord-recruiting arms are configured to extend radially from the valve-frame body, in addition to extending axially from a ventricular end of the valve-frame body (i.e., the end of the valve-frame body that is configured to be placed within the ventricle) toward an atrial end of the valve-frame body (i.e., the end of the valve-frame body that is configured to be placed within the atrium). Further typically, the chord-recruiting arms curve around the outside of the valve-frame body in a given circumferential direction of curvature (i.e., clockwise or counterclockwise). For some applications, the chord-recruiting arms are configured to have concavely rounded leading edges facing in the given circumferential direction.

Typically, there are no chord-recruiting arms disposed at a circumferential region of the valve frame corresponding to the septal leaflet of the native tricuspid valve. For example, in the non-radially-constrained configuration of the valve frame, the valve frame may include no chord-recruiting arms (or any portions thereof) around at least 20 percent (or at least 30 percent) of the circumference of the valve-frame body, in a non-radially-constrained configuration of the valve frame. For some applications, in the non-radially-constrained configuration of the valve frame, the valve frame does not include any arms (or any portions thereof) around at least 20 percent (or at least 30 percent) of the circumference of the valve-frame body, in a non-radially-constrained configuration of the valve frame. For some applications, at the circumferential region of the valve frame corresponding to the septal leaflet of the native tricuspid valve, the anchoring arm extends radially from the portion of the valve-frame body that is configured to be placed within the subject's ventricle. Typically, the anchoring arm has a different shape and/or length, and a different function from chord-recruiting arms, as described in further detail hereinbelow. For some applications, the valve frame does not include any arms (i.e., it does not include an anchoring arm or chord-recruiting arms) at the circumferential region of the valve frame corresponding to the septal leaflet of the native tricuspid valve.

For some applications, the tricuspid valve frame includes a coronary-sinus anchor that is configured to become anchored within the subject's coronary sinus. Typically, the coronary-sinus anchor is an elongate anchor that is configured, in a non-constrained configuration thereof, to extend radially from the atrial portion of the valve-frame body. Further typically, the anchor is configured be curved circumferentially with respect to the atrial portion of the valve-frame body, such as to conform with the curved shape of the coronary sinus. The coronary-sinus anchor is configured to be inserted into the ostium of the coronary sinus within the right atrium, and to then be advanced into the coronary sinus by rotation of the valve frame. The coronary sinus is typically situated in the vicinity of the septal leaflet. As such, the coronary-sinus anchor typically provides anchoring of the valve frame with respect to the native tricuspid valve at the circumferential region corresponding to the septal leaflet. Typically, the coronary-sinus anchor is constructed from a shape-memory material (e.g., a shape-memory alloy, such as nitinol and/or copper-aluminum-nickel), which is covered with a covering material, e.g., a fabric and/or a polymer (such as expanded polytetrafluoroethylene (ePTFE), or woven, knitted and/or braided polyester).

There is therefore provided, in accordance with some applications of the present invention, apparatus for use with a native tricuspid valve of a heart of a mammalian subject, the native tricuspid valve including an anterior leaflet, a posterior leaflet, and a septal leaflet, and chords extending to each of the leaflets, the apparatus including:

prosthetic valve leaflets;

a valve frame, the valve frame including:

a valve-frame body that is configured to support the prosthetic valve leaflets within the native tricuspid valve, chord-recruiting arms that are configured to extend from the valve-frame body at circumferential regions corresponding to the anterior leaflet and the posterior leaflet of the native tricuspid valve; and an anchoring arm that is configured to extend from the valve-frame body at a circumferential region corresponding to the septal leaflet of the native tricuspid valve, the anchoring arm being longer than each of the chord-recruiting arms.

In some applications, the valve-frame body further includes an atrial portion configured to be deployed in a right atrium of the subject, and the valve frame further includes a coronary-sinus anchor that extends radially from the atrial portion of the valve-frame body, the coronary-sinus anchor being configured to be inserted into a coronary sinus of the subject and to thereby anchor the valve frame with respect to the native tricuspid valve.

In some applications, the apparatus further includes a delivery catheter configured to:

deliver the valve frame to the native tricuspid valve;

deploy the chord-recruiting arms, such that the chord-recruiting arms become deployed among chords extending to each of the anterior and posterior leaflets, and the chord-recruiting arms curve around the valve-frame body circumferentially in a given circumferential direction;

deploy the anchoring arm, such that the anchoring arm becomes deployed among chords extending to the septal leaflet, and the anchoring arm curves around the valve-frame body circumferentially in the given circumferential direction; and rotate at least a portion of the valve frame, in the given circumferential direction, such as:

to cause the chord-recruiting arms to (a) pull the anterior and posterior leaflets radially inward toward the valve frame, and (b) twist the anterior and posterior leaflets around the valve frame, by recruiting and deflecting at least a portion of the chords that extend to the anterior and posterior leaflets, and to cause the anchoring arm to become anchored within the chords that extend toward the septal leaflet.

In some applications, the delivery catheter is configured to cause the valve-frame body to radially expand, such as to trap the anterior and posterior leaflets in a partially closed and twisted configuration, to thereby at least partially seal a space between the native tricuspid valve and the valve frame.

In some applications, the anchoring arm is not configured to manipulate a shape of the septal leaflet in a manner in which the chord-recruiting arms are configured to manipulate shapes of the anterior and posterior leaflets by the portion of the valve frame being rotated.

In some applications, in a non-radially-constrained configuration of the valve frame, the chord-recruiting arms encompass less than 80 percent of a circumference of the valve-frame body.

In some applications, in the non-radially-constrained configuration of the valve frame, the chord-recruiting arms encompass more than 40 percent of the circumference of the valve-frame body.

In some applications, the anchoring arm and the chord-recruiting arms are configured to assume chord-deployment configurations by being released from their radially constrained configurations while a portion of the valve frame from which the arms extend is still maintained in a radially-constrained configuration, and the anchoring arm is configured to become deployed among chords that extend to the septal leaflet by assuming its chord-deployment configuration, and the chord-recruiting arms are configured to become deployed among chords that extend to the anterior leaflet and among chords that extend to the posterior leaflet by assuming their chord-deployment configurations.

In some applications, in the chord-deployment configurations of the arms, a ratio of the length of the anchoring arm to lengths of each of the chord recruiting arms when measured along a center of each of the arms from a base of the arm to a tip of the arm is greater than 4:3.

In some applications, in the chord-deployment configurations of the arms, a ratio of the length of the anchoring arm to lengths of each of the chord recruiting arms when measured along the center of each of the arms from the base of the arm to the tip of the arm is greater than 2:1.

There is further provided, in accordance with some applications of the present invention, apparatus for use with a native tricuspid valve of a heart of a mammalian subject, the native tricuspid valve including an anterior leaflet, a posterior leaflet, and a septal leaflet, and chords extending to each of the leaflets, the apparatus including:

prosthetic valve leaflets;

a valve frame, the valve frame including:

a valve-frame body that is configured to support the prosthetic valve leaflets within the native tricuspid valve; and chord-recruiting arms that are configured to extend from the valve-frame body at circumferential regions corresponding to the anterior leaflet and the posterior leaflet of the native tricuspid valve, the valve frame not including any arms extending from the valve-frame body at a circumferential region corresponding to the septal leaflet of the native tricuspid valve.

In some applications, the valve-frame body includes an atrial portion configured to be deployed in a right atrium of the subject, and the valve frame further includes a coronary-sinus anchor that extends radially from the atrial portion of the valve-frame body, the coronary-sinus anchor being configured to be inserted into a coronary sinus of the subject and to thereby anchor the valve frame with respect to the native tricuspid valve.

In some applications, the apparatus further includes a delivery catheter configured to: deliver the valve frame to the native tricuspid valve;

deploy the chord-recruiting arms, such that the chord-recruiting arms become deployed among chords extending to each of the anterior and posterior leaflets, and the chord-recruiting arms curve around the valve-frame body circumferentially in a given circumferential direction; and rotate at least a portion of the valve frame, in the given circumferential direction, such as to cause the chord-recruiting arms to (a) pull the anterior and posterior leaflets radially inward toward the valve frame, and (b) twist the anterior and posterior leaflets around the valve frame, by recruiting and deflecting at least a portion of the chords that extend to the anterior and posterior leaflets.

In some applications, in a non-radially-constrained configuration of the valve frame, the chord-recruiting arms encompass less than 80 percent of a circumference of the valve-frame body.

In some applications, in a non-radially-constrained configuration of the valve frame, the chord-recruiting arms encompass more than 40 percent of the circumference of the valve-frame body.

In some applications, in a non-radially-constrained configuration of the valve frame, the valve frame does not include any chord-recruiting arms extending from the valve-frame body around at least 20 percent of a circumference of the valve-frame body In some applications, in the non-radially-constrained configuration of the valve frame, the valve frame does not include any chord-recruiting arms extending from the valve-frame body around at least 30 percent of the circumference of the valve-frame body In some applications, the chord-recruiting arms are configured to extend from a longitudinal location along the valve-frame body and in a non-radially-constrained configuration of the valve frame, at the longitudinal location along the valve-frame body, the valve frame does not include any chord-recruiting arms around at least 20 percent of a circumference of the valve-frame body.

In some applications, in the non-radially-constrained configuration of the valve frame, at the longitudinal location along the valve-frame body, the valve frame does not include any chord-recruiting arms around at least 30 percent of a circumference of the valve-frame body.

In some applications, the valve-frame body includes a ventricular portion configured to be deployed in a right ventricle of the subject, and the chord-recruiting arms are configured to extend from a distal end of the ventricular portion of the valve-frame body.

There is further provided, in accordance with some applications of the present invention, apparatus for use with a native tricuspid valve of a heart of a mammalian subject, the native tricuspid valve including an anterior leaflet, a posterior leaflet, and a septal leaflet, and chords extending to each of the leaflets, the apparatus including:

prosthetic valve leaflets;

a valve frame, the valve frame including:

a valve-frame body that is configured to support the prosthetic valve leaflets within the native tricuspid valve, the valve-frame body including an atrial portion configured to be disposed in a right atrium of the subject; and a coronary-sinus anchor that extends radially from the atrial portion of the valve-frame body, the coronary-sinus anchor being configured to be inserted into a coronary sinus of the subject and to thereby anchor the valve frame with respect to the native tricuspid valve.

In some applications, the valve frame further includes:

chord-recruiting arms that are configured to extend from the valve-frame body at circumferential regions corresponding to the anterior leaflet and the posterior leaflet of the native tricuspid valve; and an anchoring arm that is configured to extend from the valve-frame body at a circumferential region corresponding to the septal leaflet of the native tricuspid valve, the anchoring arm being longer than each of the chord-recruiting arms.

In some applications, in a non-radially-constrained configuration of the valve frame, the chord-recruiting arms encompass less than 80 percent of a circumference of the valve-frame body.

In some applications, in the non-radially-constrained configuration of the valve frame, the chord-recruiting arms encompass more than 40 percent of the circumference of the valve-frame body.

In some applications, the anchoring arm and the chord-recruiting arms are configured to assume chord-deployment configurations by being released from their radially constrained configurations while a portion of the valve frame from which the arms extend is still maintained in a radially-constrained configuration, and the anchoring arm is configured to become deployed among chords that extend to the septal leaflet by assuming its chord-deployment configuration, and the chord-recruiting arms are configured to become deployed among chords that extend to the anterior leaflet and among chords that extend to the posterior leaflet by assuming their chord-deployment configurations.

In some applications, in the chord-deployment configurations of the arms, a ratio of the length of the anchoring arm to lengths of each of the chord recruiting arms when measured along a center of each of the arms from a base of the arm to a tip of the arm is greater than 4:3.

In some applications, in the chord-deployment configurations of the arms, a ratio of the length of the anchoring arm to lengths of each of the chord recruiting arms when measured along the center of each of the arms from the base of the arm to the tip of the arm is greater than 2:1.

In some applications, the valve frame further includes chord-recruiting arms that are configured to extend from the valve-frame body at circumferential regions corresponding to the anterior leaflet and the posterior leaflet of the native tricuspid valve, and the valve frame does not include any arms extending from the valve-frame body at a circumferential region corresponding to the septal leaflet of the native tricuspid valve In some applications, in a non-radially-constrained configuration of the valve frame, the chord-recruiting arms encompass less than 80 percent of a circumference of the valve-frame body.

In some applications, in the non-radially-constrained configuration of the valve frame, the chord-recruiting arms encompass more than 40 percent of the circumference of the valve-frame body.

In some applications, in a non-radially-constrained configuration of the valve frame, the valve frame does not include any chord-recruiting arms extending from the valve-frame body around at least 20 percent of a circumference of the valve-frame body.

In some applications, in the non-radially-constrained configuration of the valve frame, the valve frame does not include any chord-recruiting arms extending from the valve-frame body around at least 30 percent of the circumference of the valve-frame body.

In some applications, the chord-recruiting arms are configured to extend from a longitudinal location along the valve-frame body and, in a non-radially-constrained configuration of the valve frame, at the longitudinal location along the valve-frame body, the valve frame does not include any chord-recruiting arms around at least 20 percent of a circumference of the valve-frame body.

In some applications, in the non-radially-constrained configuration of the valve frame, at the longitudinal location along the valve-frame body, the valve frame does not include any chord-recruiting arms around at least 30 percent of a circumference of the valve-frame body.

In some applications, the valve-frame body includes a ventricular portion configured to be deployed in a right ventricle of the subject, and the chord-recruiting arms are configured to extend from a distal end of the ventricular portion of the valve-frame body.

The present invention will be more fully understood from the following detailed description of applications thereof, taken together with the drawings, in which:

DETAILED DESCRIPTION OF EMBODIMENTS

Figure 1:
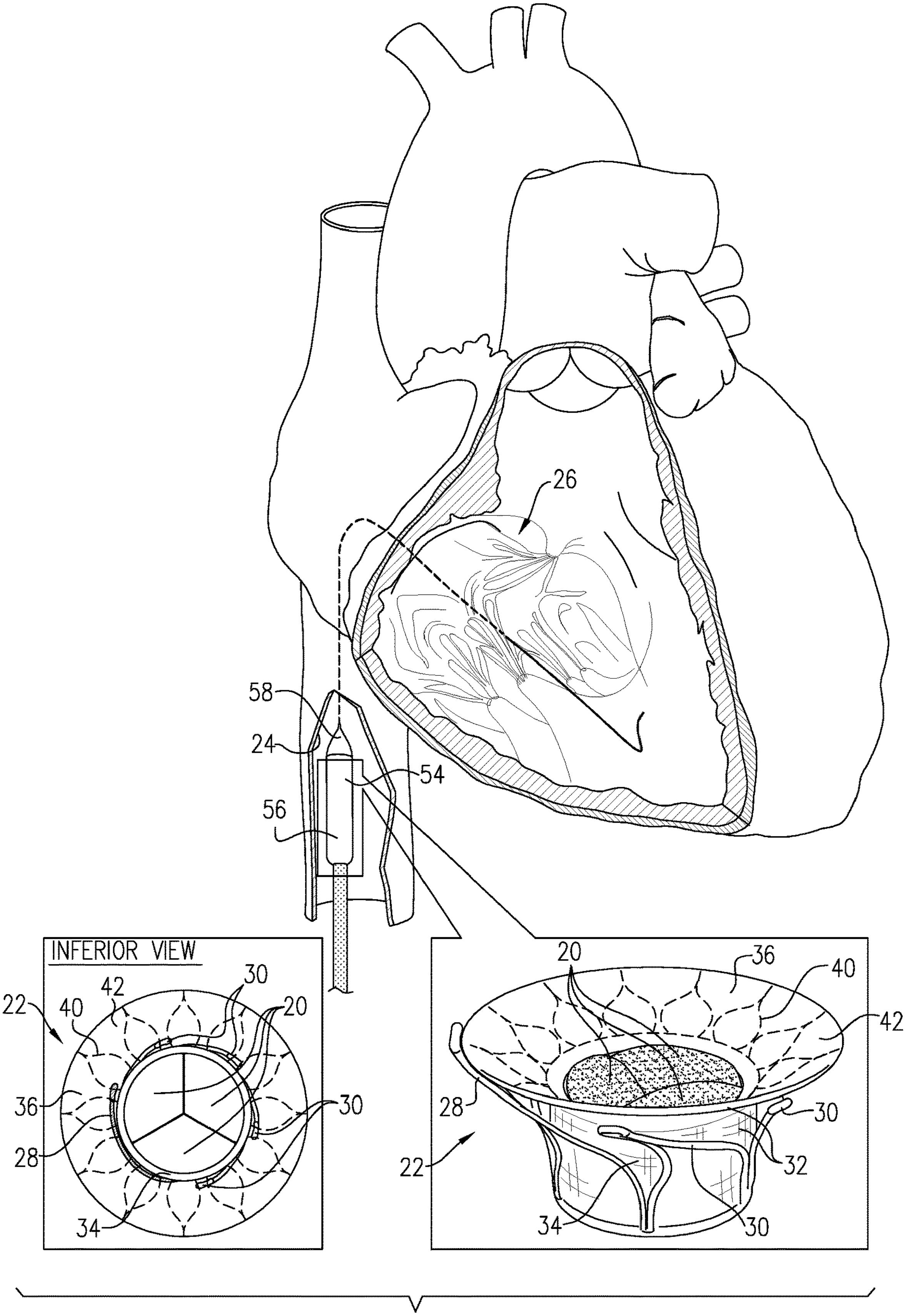
FIG. 1 is a schematic illustration of a prosthetic tricuspid valve frame, which supports prosthetic valve leaflets, being delivered through a subject's vena cava toward the subject's native tricuspid valve, in accordance with some applications of the present invention.

Reference is now made to FIG. 1, which is a schematic illustration of prosthetic tricuspid valve leaflets 20 and a prosthetic tricuspid valve frame 22 being delivered through a subject's vena cava 24 toward the subject's native tricuspid valve 26. The prosthetic tricuspid valve frame 22 is typically delivered through the subject's inferior or superior vena cava. Typically, the tricuspid valve frame includes an anchoring arm 28 at a circumferential region corresponding to the septal leaflet of the native tricuspid valve and includes a plurality of chord-recruiting arms 30 at circumferential regions corresponding to the anterior and posterior leaflets of the native tricuspid valve. For some applications, the prosthetic tricuspid valve frame includes a valve-frame body 32 that defines a ventricular portion 34 (which upon deployment is configured to be disposed within the subject's right ventricle), and an atrial portion 36 (which upon deployment is configured to be disposed within the subject's right atrium). For some applications, the atrial portion comprises a flange that is configured to contact the atrial side of the native valve annulus. Prosthetic tricuspid valve frame 22 typically supports a plurality of prosthetic tricuspid valve leaflets 20 (e.g., two leaflets, or three leaflets, as shown), which are sutured or otherwise coupled to the valve-frame body.

Typically, tricuspid valve frame 22 is made of a shape-memory material 40 (e.g., a shape-memory alloy, such as nitinol and/or copper-aluminum-nickel), which is covered on one or both sides with a covering material 42, e.g., a fabric and/or a polymer (such as expanded polytetrafluoroethylene (ePTFE), or woven, knitted and/or braided polyester). Typically, the shape-memory material of the valve frame is shaped into a stent-like structure that comprises struts and/or cells of the shape-memory material. The covering material is typically coupled to the shape-memory material via stitches.

Typically, in a non-constrained configuration of prosthetic tricuspid valve frame 22, chord-recruiting arms 30 extend radially from a portion of valve-frame body 32 that is configured to be placed within the subject's ventricle. For some applications, in a non-radially-constrained configuration of the valve frame, the chord-recruiting arms encompass more than 40 percent of the circumference of the valve-frame body (e.g., more than 60 percent of the circumference of the valve-frame body), and/or less than 80 percent of the of the circumference of the valve-frame body (e.g., less than 70 percent of the circumference of the valve-frame body). Typically, the chord-recruiting arms are configured to be disposed at circumferential regions corresponding to the anterior and posterior leaflets of the native tricuspid valve, and are configured to recruit the chords of the aforementioned leaflets, as described in further detail hereinbelow. Typically, the chord-recruiting arms are configured to extend radially from the valve-frame body, in addition to extending axially from a ventricular end of the valve-frame body (i.e., the end of the valve-frame body that is configured to be placed within the ventricle) toward an atrial end of the valve-frame body (i.e., the end of the valve-frame body that is configured to be placed within the atrium). Further typically, the chord-recruiting arms curve around the outside of the valve-frame body in a given circumferential direction of curvature (i.e., clockwise or counterclockwise). For some applications, the chord-recruiting arms are configured to have concavely rounded leading edges facing in the given circumferential direction.

Figure 6:
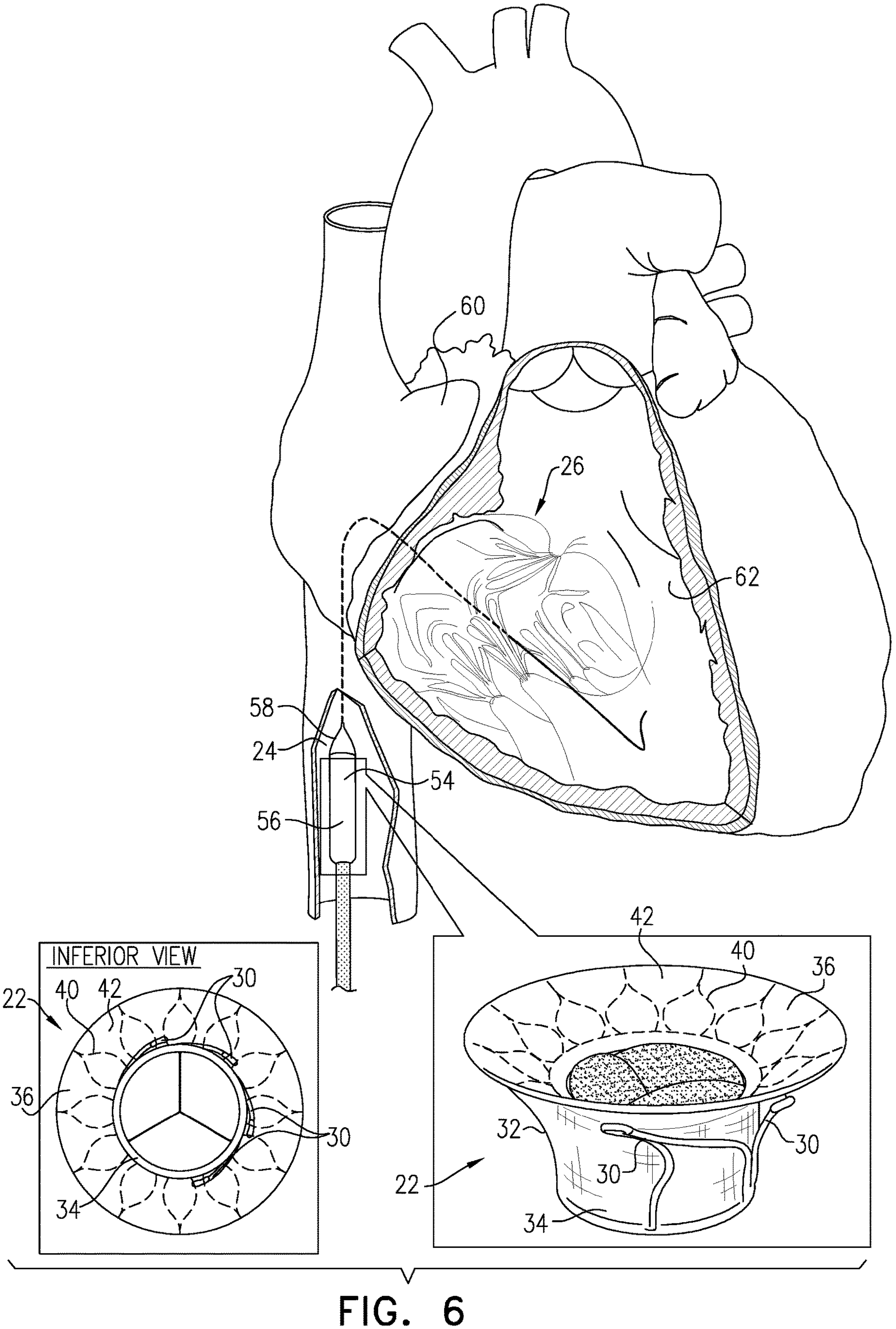
FIGS. 6 and 7 are schematic illustrations of respective steps of the deployment of a prosthetic tricuspid valve frame at a subject's native tricuspid valve, in accordance with some alternative applications of the present invention.
Figure 7:
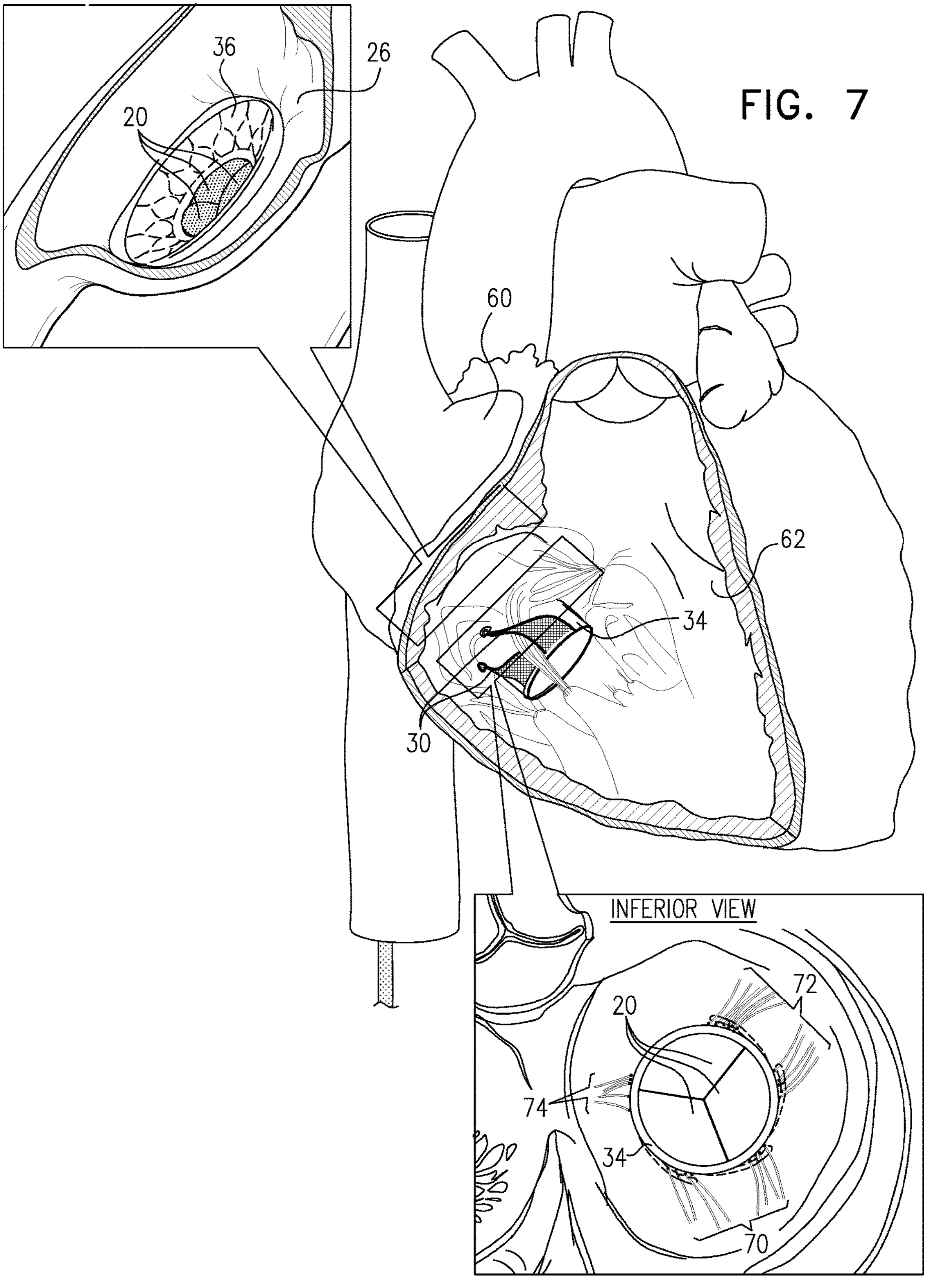

Typically, there are no chord-recruiting arms disposed at a circumferential region of the valve frame corresponding to the septal leaflet of the native tricuspid valve. For example, the valve frame may include no chord-recruiting arms (or any portions thereof) around at least 20 percent (or at least 30 percent) of the circumference of the valve-frame body, in a non-radially-constrained configuration of the valve frame. For some applications, in the non-radially-constrained configuration of the valve frame, the valve frame does not include any arms (or any portions thereof) around at least 20 percent (or at least 30 percent) of the circumference of the valve-frame body, in a non-radially-constrained configuration of the valve frame. (As noted above, the chord-recruiting arms typically curve around the outside of the valve-frame body. For some applications, at the longitudinal location along the valve-frame body from which the chord-recruiting arms extend from the valve frame body (e.g., at the distal end of the ventricular portion of the valve-frame body) the valve frame includes no chord-recruiting arms (or any arms, or any portions thereof) around at least 20 percent (or at least 30 percent) of the circumference of the valve-frame body. However, owing to the curvature of the chord-recruiting arms around the outside of the valve-frame body, at a different location along the valve-frame body, the chord-recruiting arms may extend around a greater portion of the circumference of the valve-frame body.) For some applications, at the circumferential region of the valve frame corresponding to the septal leaflet of the native tricuspid valve, anchoring arm 28 extends radially from the portion of valve-frame body 32 that is configured to be placed within the subject's ventricle, as shown in FIGS. 1-5. Typically, anchoring arm 28 has a different shape and/or length, and a different function from chord-recruiting arms 30, as described in further detail hereinbelow. For some applications, the valve frame does not include any arms (i.e., it does not include an anchoring arm or chord-recruiting arms) at the circumferential region of the valve frame corresponding to the septal leaflet of the native tricuspid valve, as shown in FIGS. 6-7.

Typically, prosthetic tricuspid valve frame 22 is delivered to the native tricuspid valve, using a delivery catheter 50 (shown in FIG. 2, for example), which is inserted over a guidewire 52. The delivery catheter is configured to maintain prosthetic tricuspid valve frame 22 in a radially-constrained configurations (i.e., a "crimped" configuration) during the delivery. For some applications, the delivery catheter includes a capsule 54 that is configured to house the prosthetic tricuspid valve frame 22 in its radially-constrained configuration. For some applications, the capsule includes a proximal capsule portion 56 (which is configured to maintain a proximal portion of the prosthetic tricuspid valve frame in a radially-constrained configuration by covering the proximal portion), and a distal capsule portion 58 (which is configured to maintain a distal portion of the prosthetic tricuspid valve frame in a radially-constrained configuration by covering the distal portion). Alternatively, the delivery catheter includes a different housing component that is configured to house the prosthetic tricuspid valve frame 22 in its radially-constrained configuration. For example, the delivery catheter may include a one-piece capsule, and/or a different housing element.

It is noted that the term "distal" and related terms, when used with reference to a device or a portion thereof, should be interpreted to mean an end of the device or the portion thereof that, when inserted into a subject's body, is typically further from the location through which the device is inserted into the subject's body. The term "proximal" and related terms, when used with reference to a device or a portion thereof, should be interpreted to mean an end of the device or the portion thereof that, when inserted into a subject's body, is typically closer to the location through which the device is inserted into the subject's body. It is further noted that the enlarged portions of FIG. 1 show respective views of prosthetic tricuspid valve frame in its non-radially-constrained configuration, for illustrative purposes.

Figure 2:
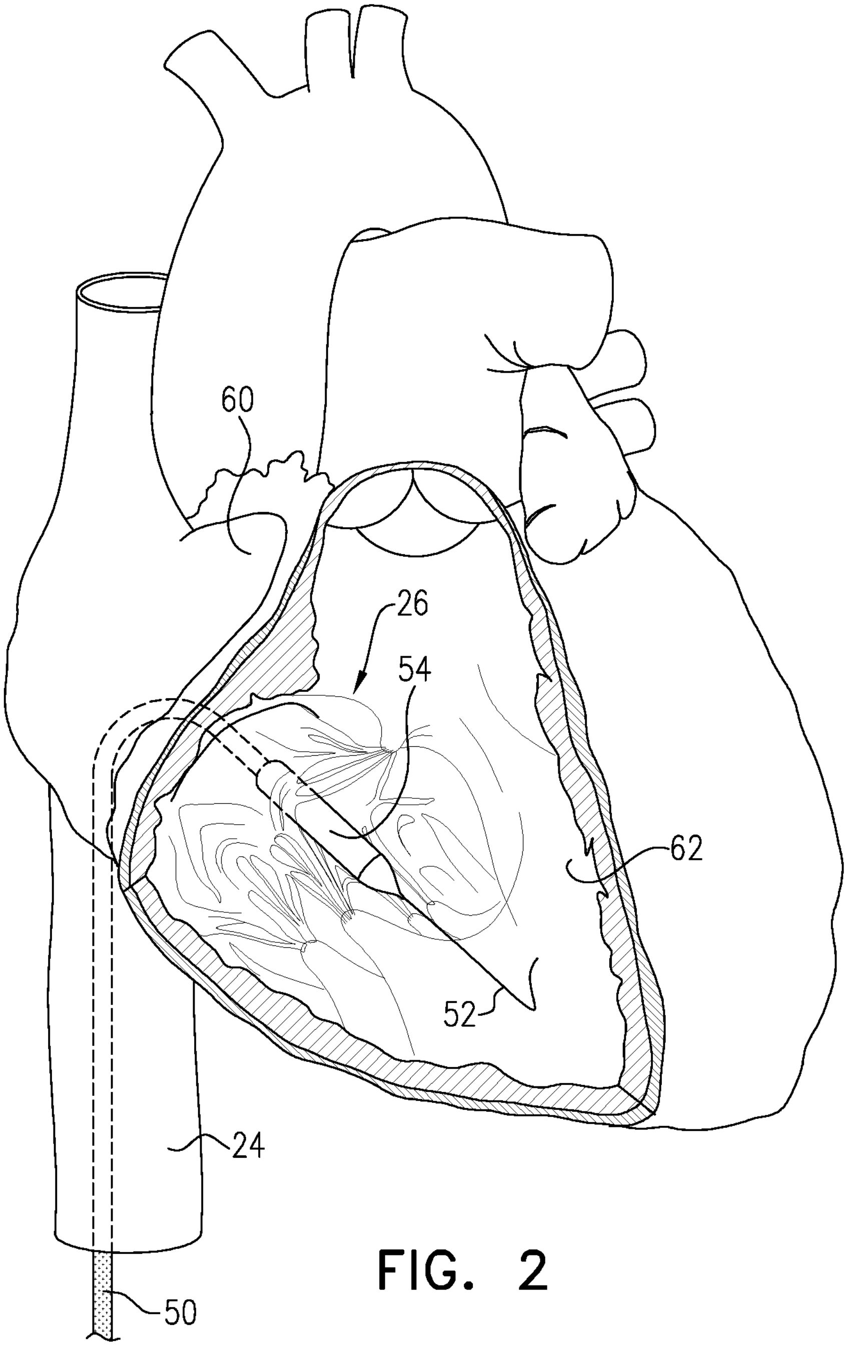
FIGS. 2, 3, 4, and 5 are schematic illustrations of respective steps of the deployment of the prosthetic tricuspid valve frame at the subject's native tricuspid valve, in accordance with some applications of the present invention.
Figure 3:
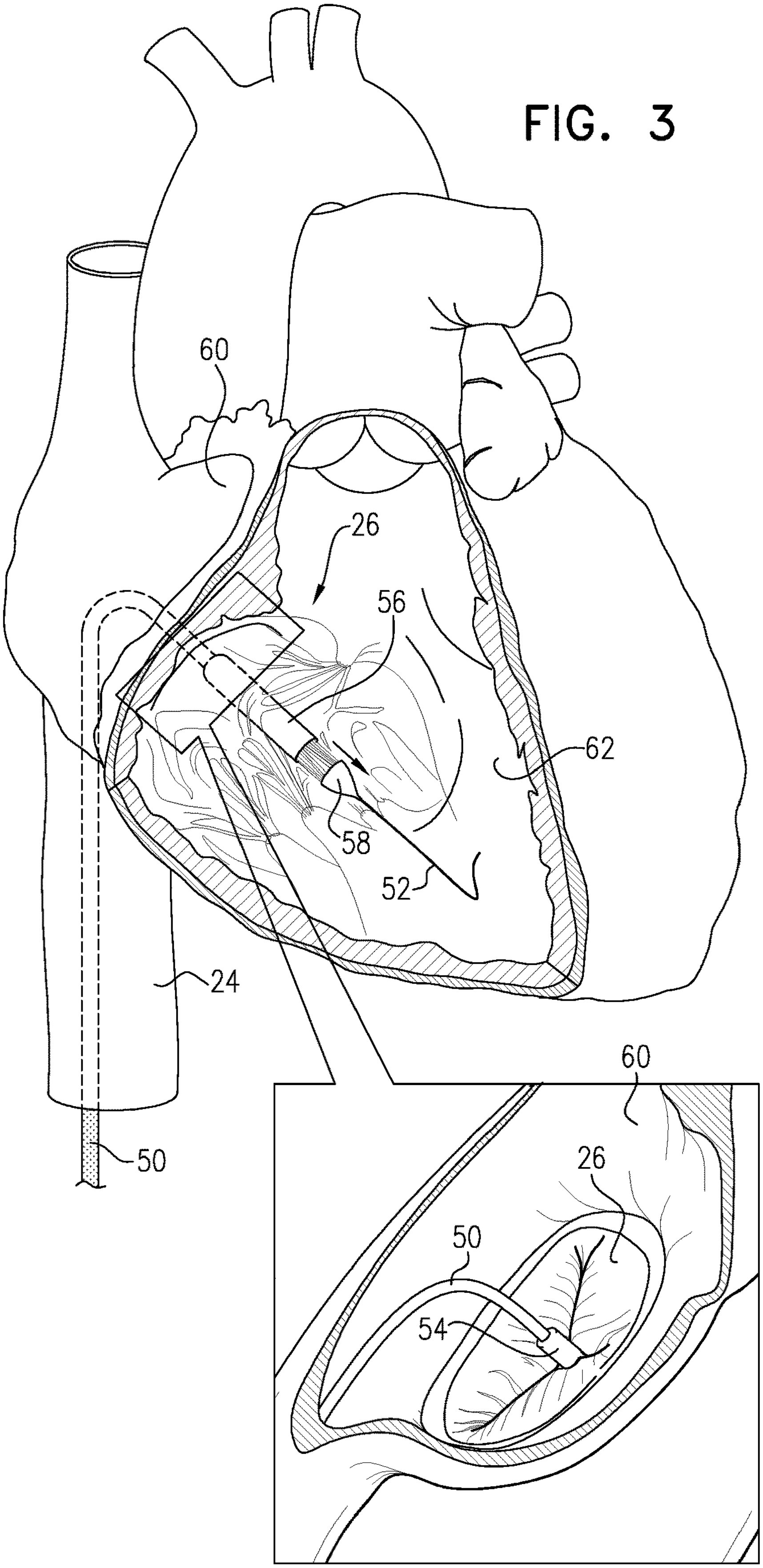
Figure 4:
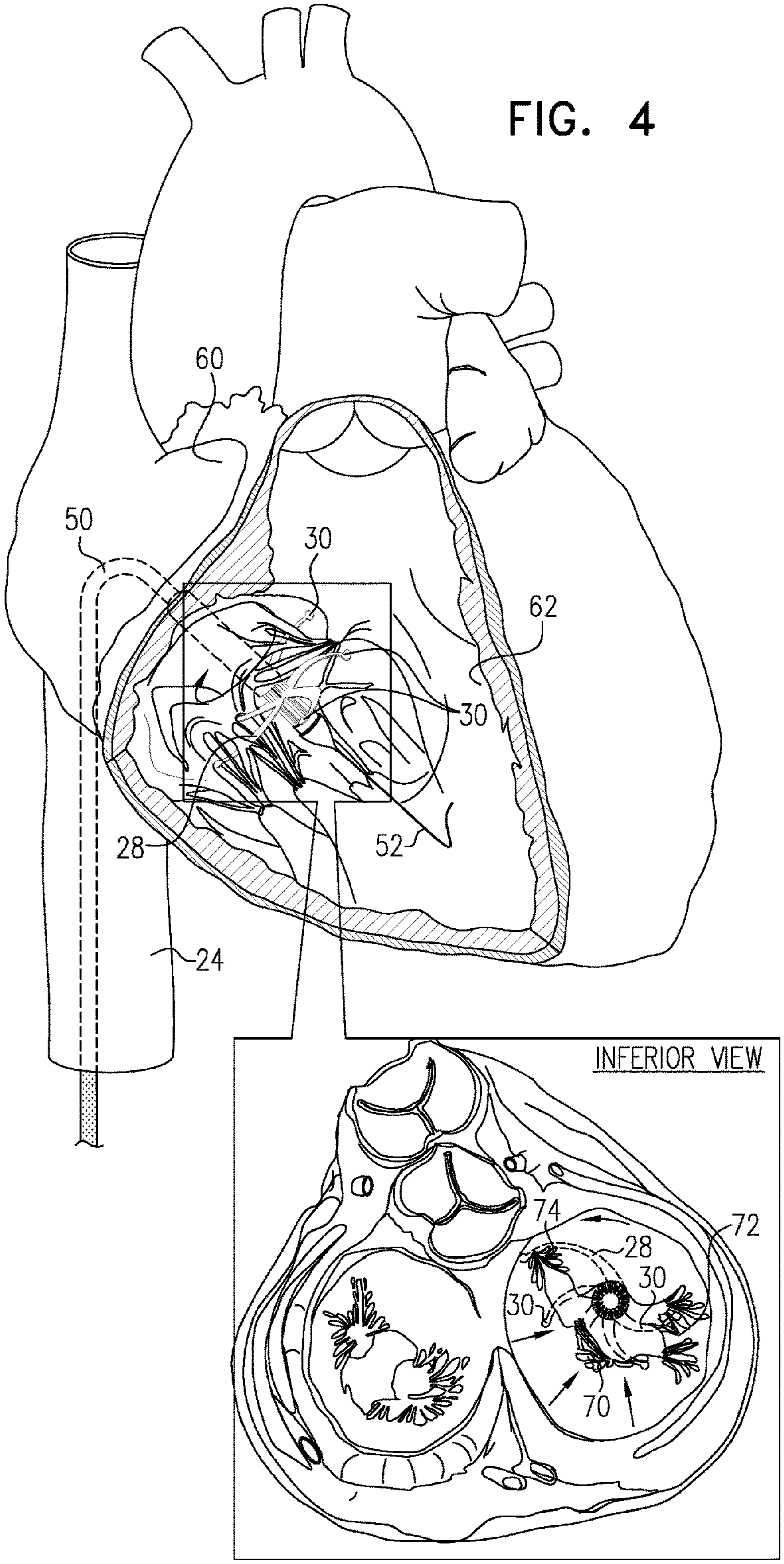

Reference is now made to FIGS. 2, 3, 4, and 5 are schematic illustrations of respective steps of the deployment of prosthetic tricuspid valve leaflets 20 and the prosthetic tricuspid valve frame 22 at the subject's native tricuspid valve 26, in accordance with some applications of the present invention. As shown in FIG. 2, delivery catheter 50 is typically advanced to the subject's right atrium 60 and then into the subject's right ventricle 62, such that capsule 54 of the delivery catheter traverses the subject's native tricuspid valve 26. For some applications, anchoring arm 28 and chord-recruiting arms 30 are then released from their radially constrained configurations. For example, as indicated by the arrows in FIG. 3, distal capsule portion 58 may be advanced distally and/or proximal capsule portion may be retracted proximally such that anchoring arm 28 and chord-recruiting arms 30 are then released from their radially constrained configurations. Alternatively, the prosthetic tricuspid valve frame may be housed in a delivery catheter having a different housing element (e.g., a one-piece capsule), and the release of anchoring arm 28 and chord-recruiting arms 30 from their radially constrained configurations may be modified accordingly. The transition from FIG. 3 to FIG. 4 schematically illustrates the release of anchoring arm 28 and chord-recruiting arms 30 from their radially constrained configurations.

Typically, anchoring arm 28 and chord-recruiting arms 30 are released from their radially constrained configurations while a portion of the valve frame from which the arms extend (which is typically ventricular portion 34) is still maintained in a radially-constrained configuration, as shown in FIG. 4. For some applications, in this configuration (referred to herein as the "chord-deployment configurations" of the anchoring arm 28 and chord-recruiting arms 30), anchoring arm 28 and chord-recruiting arms 30 extend radially from the valve-frame body and are also shaped such as to curve around the valve frame circumferentially in a given direction (i.e., clockwise or counterclockwise). Typically, the length of the anchoring arm is greater than that of the chord-recruiting arms. For example, a ratio of the length of the anchoring arm to that of each of the chord recruiting arms (when measured along the center of each of the arms from the base of the arm (i.e., the location at which the arm is attached to valve frame) to the tip of the arm) is typically greater than 4:3, greater than 3:2, or greater than 2:1.

As described in the Background section, the tricuspid valve includes three leaflets: the septal leaflet, the anterior leaflet, and the posterior leaflet. Each of the valve leaflets is attached to the tricuspid valve annulus, which defines the tricuspid valve orifice. The leaflets are connected to papillary muscles within the right ventricle, by chords. Typically, the native tricuspid valve apparatus is structured such that chords 70 extending to the anterior leaflet from the anterior papillary muscle as well as chords 72 extending to the posterior leaflet from the posterior papillary muscle are relatively long and flexible, whereas chords 74 extending to the septal leaflet from the septal papillary muscle (or from the wall of the right ventricle) are relatively short and stiff. As described hereinabove, chord-recruiting arms 30 are configured to be disposed at circumferential regions corresponding to the anterior and posterior leaflets of the native tricuspid valve. Typically, upon being released from their radially-constrained configurations (i.e., the stage of the deployment shown in FIG. 4), the chord-recruiting arms assume their chord-deployment configurations and become deployed among chords 70 (which extend to the anterior leaflet from the anterior papillary muscle) and among chords 72 (which extend to the posterior leaflet from the posterior papillary muscle). At the circumferential region of the valve frame corresponding to the septal leaflet of the native tricuspid valve, anchoring arm 28 assumes its chord-deployment configuration and extends radially from the portion of valve-frame body 32. Owing to the short length of chords 74 (which extend to the septal leaflet from the septal papillary muscle or from the wall of the right ventricle), in order for the anchoring arm to deploy among these chords, the anchoring arm is typically made to be longer than the chord-recruiting arms, as described hereinabove.

Typically, subsequent to anchoring arm 28 and chord-recruiting arms 30 being deployed among respective sets of chords (and while anchoring arm 28 and chord-recruiting arms 30 are still in their chord-deployment configurations), at least a portion of the valve frame is rotated. For some applications, the valve frame is rotated in the circumferential direction in which anchoring arm 28 and chord-recruiting arms 30 circumferentially curve around the valve frame. Typically, the rotation of the valve frame causes chord-recruiting arms 30 to (a) pull the anterior and posterior leaflets radially inward toward the valve frame, and (b) twist the anterior and posterior leaflets around the valve frame, by recruiting and deflecting at least a portion of chords 70 and 72. Further typically, the rotation of the valve frame causes anchoring arm 28 to become anchored with respect to chords 74. It is noted that the septal leaflet is typically less flexible and smaller than the anterior and posterior leaflets. Therefore, the anchoring arm typically is not used to manipulate the shape of the septal leaflet in the manner in which the chord-recruiting arms are configured to manipulate the shapes of the anterior and posterior leaflets.

Subsequent to anchoring arm 28 and chord-recruiting arms 30 being deployed among respective sets of chords and the valve frame having been rotated, valve-frame body 32 (i.e., ventricular portion 34 and atrial portion 36 of the valve-frame body) is allowed to assume its non-radially-constrained configuration. For some applications, the atrial portion is allowed to assume its non-radially-constrained configuration by releasing the atrial portion from the delivery catheter, e.g., by further retracting proximal capsule portion 56. For some applications, the ventricular portion is allowed to assume its non-radially-constrained configuration by releasing the ventricular portion from the delivery catheter, e.g., by further advancing distal capsule portion 58. Alternatively, the valve frame may be housed in a delivery catheter having a different housing component (e.g., a one-piece capsule), and the release of ventricular portion 34 and atrial portion 36 of the valve-frame body from their radially constrained configurations may be modified accordingly.

Figure 5:
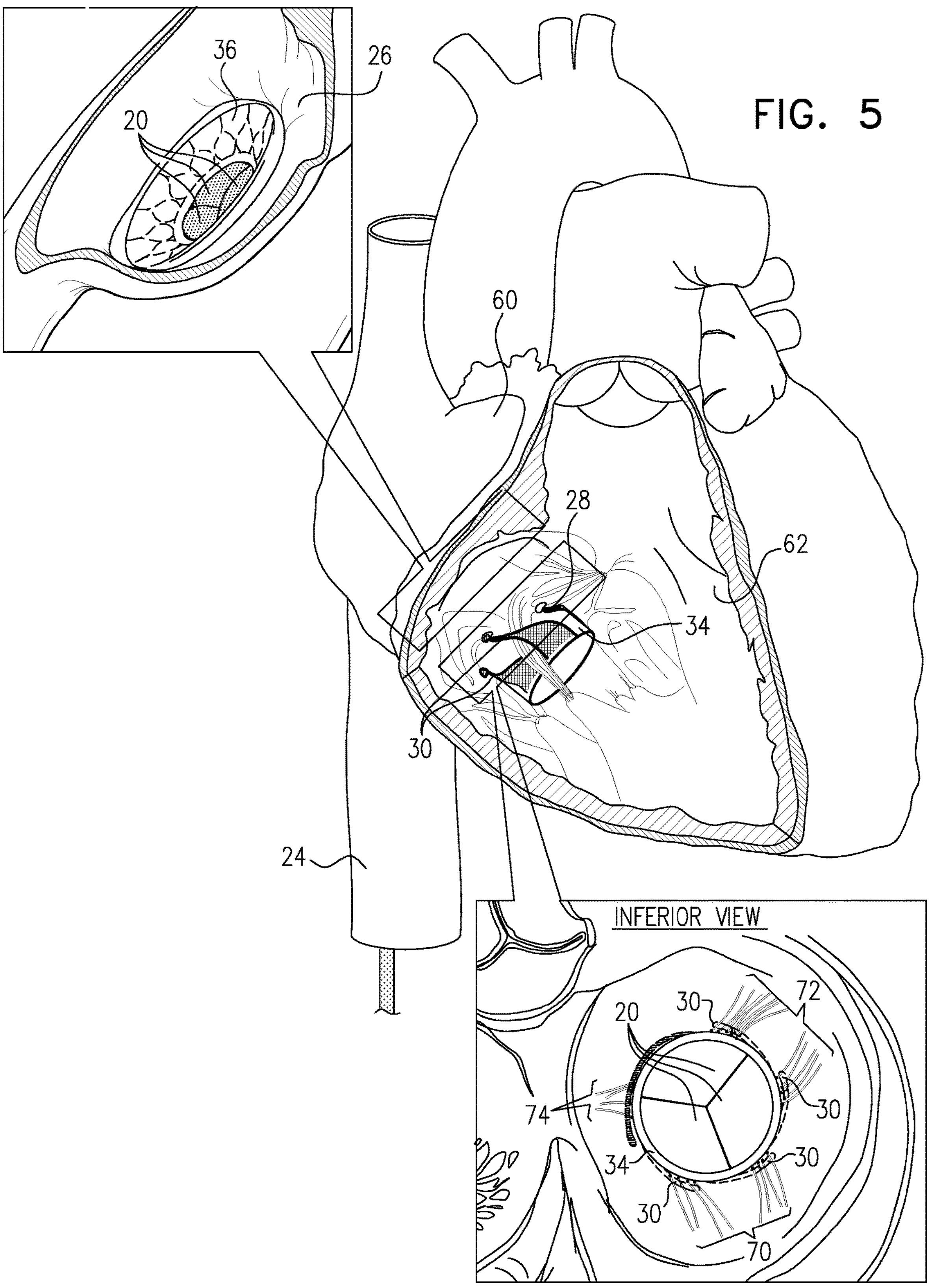

FIG. 5 shows both ventricular portion 34 and atrial portion 36 of valve-frame body 32 in their non-radially-constrained (i.e., radially-expanded) configurations. Typically, by the valve-frame body assuming its non-radially-constrained configuration, the valve-frame body is configured to trap the anterior and posterior leaflets in a partially closed and twisted configuration, to thereby at least partially seal a space between the native prosthetic valve and the valve frame. Further typically, as shown, the valve frame is typically anchored to the native tricuspid valve by (a) chords 70 and chords 72 being held between chord-recruiting arms 30 and the valve-frame body, and/or (b) chords 74 being held between anchoring arm 28 and the valve-frame body.

For some applications, the release of the valve-frame body causes the shapes of the anchoring arm and/or the chord-recruiting arms to change from their chord-deployment configurations to configurations that are referred to herein as the "deployed configurations" of anchoring arm 28 and chord-recruiting arms 30. (It is noted that the deployed configurations of the anchoring arm and the chord-recruiting arms are typically the same as their non-radially-constrained configurations.) For example, as shown in the transition from FIG. 4 to FIG. 5, the bases of the anchoring arm and/or the chord-recruiting arms may widen. Alternatively or additionally, the anchoring arm and/or the chord-recruiting arms may become more axially oriented. Typically, even in their deployed configurations, the anchoring arm and/or the chord-recruiting arms extend radially from the valve-frame body and curve around the valve-frame body circumferentially. Subsequent to the above described steps being performed, delivery catheter 50 is typically then retracted in its entirety from the subject's right atrium.

Reference is now made to FIGS. 6 and 7, which are schematic illustrations of respective steps of the deployment of prosthetic tricuspid valve leaflets 20 and prosthetic tricuspid valve frame 22 at a subject's native tricuspid valve, in accordance with some applications of the present invention. Prosthetic tricuspid valve frame 22 as shown in FIGS. 6 and 7 is generally similar to that shown in FIGS. 1-5. However, in accordance with some applications of the present invention, the valve frame lacks any chord-recruiting or anchoring arms at a circumferential region corresponding to the septal leaflet. As depicted in FIG. 7, the valve frame typically includes chord-recruiting arms 30 at circumferential regions corresponding to the anterior and posterior leaflets. The sizes, structure and function of the chord-recruiting arms is typically generally similar to that described hereinabove with reference to FIGS. 1-5. For example, chord-recruiting arms 30 are typically configured such that the rotation of the valve frame causes the chord-recruiting arms to (a) pull the anterior and posterior leaflets radially inward toward the valve frame, and (b) twist the anterior and posterior leaflets around the valve frame, by recruiting and deflecting at least a portion of chords 70 and 72. Alternatively or additionally, the valve frame is anchored to the native tricuspid valve by chords 70 and chords 72 being held between the chord-recruiting arms and the valve-frame body, as shown in FIG. 7. For such applications, there is no arm extending from the ventricular portion of the valve frame at a circumferential region corresponding to the septal leaflet that is configured to anchor the valve frame with respect to the septal leaflet and/or chords 74. For some applications, an alternative anchoring mechanism is used to anchor the valve frame at the circumferential region corresponding to the septal leaflet, for example, as described hereinbelow with reference to FIG. 8.

Figure 8:
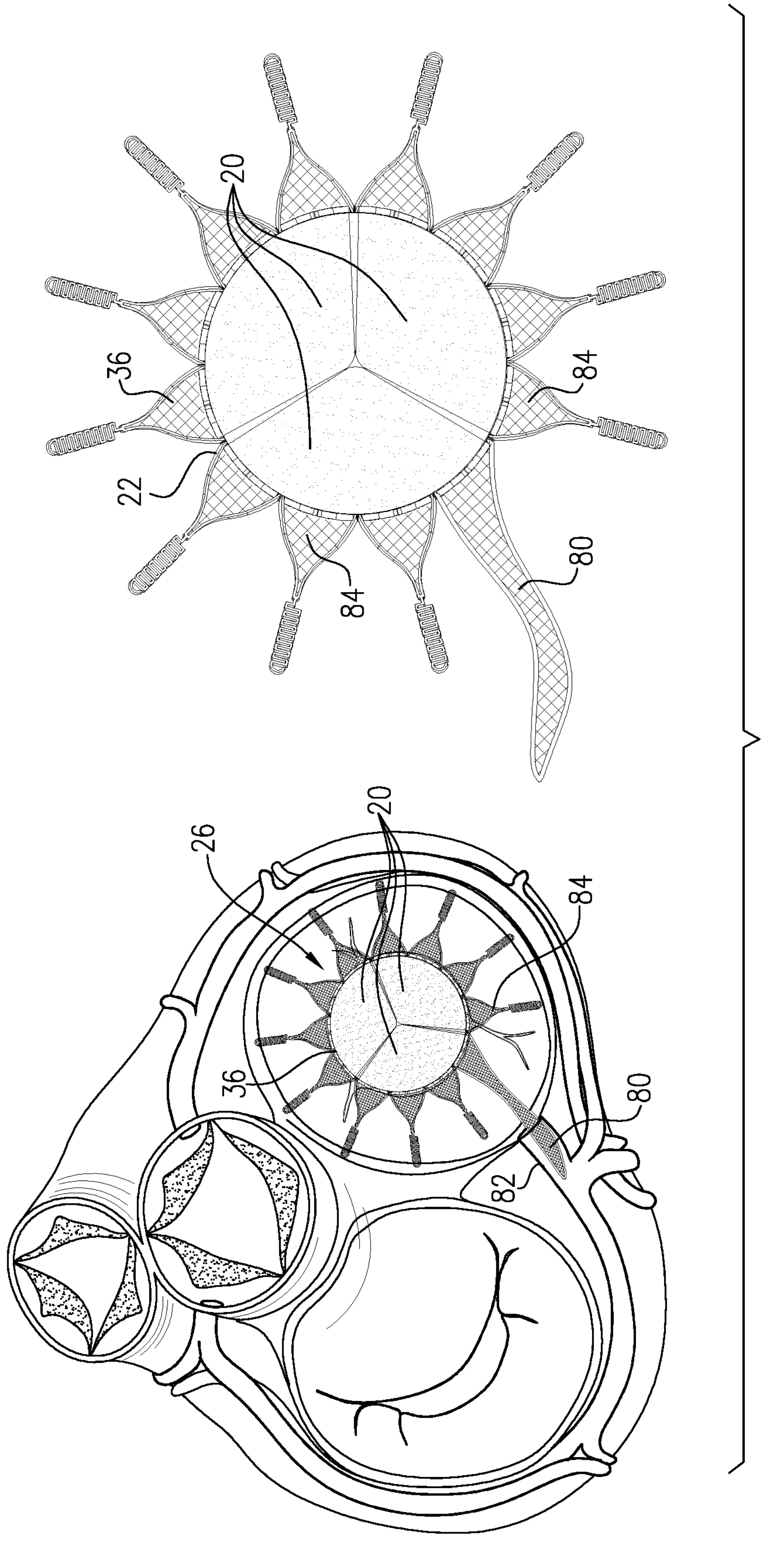
FIG. 8 is a schematic illustration of a tricuspid valve frame that includes a coronary-sinus anchor that is configured to become anchored within the subject's coronary sinus, in accordance with some applications of the present invention.

Reference is now made to FIG. 8, which is a schematic illustration of a superior view of a native tricuspid valve 26 alongside a tricuspid valve frame 22 that includes a coronary-sinus anchor 80 that is configured to become anchored within the subject's coronary sinus 82, in accordance with some alternative applications of the present invention. Typically, coronary-sinus anchor 80 is an elongate anchor that is configured, in a non-constrained configuration thereof, to extend radially from atrial portion 36 of valve-frame body 32. Further typically, the anchor is configured be curved circumferentially with respect to the atrial portion 36 of valve-frame body 32, such as to conform with the curved shape of the coronary sinus. The coronary-sinus anchor is configured to be inserted into the ostium of the coronary sinus within the right atrium, and to then be advanced into the coronary sinus by rotation of the valve frame. As shown in FIG. 8, the coronary sinus is typically situated in the vicinity of the septal leaflet. As such, the coronary-sinus anchor typically provides anchoring of the valve frame with respect to the native tricuspid valve at the circumferential region corresponding to the septal leaflet. Typically, the coronary-sinus anchor is constructed from a shape-memory material (e.g., a shape-memory alloy, such as nitinol and/or copper-aluminum-nickel), which is covered with a covering material, e.g., a fabric and/or a polymer (such as expanded polytetrafluoroethylene (ePTFE), or woven, knitted and/or braided polyester).

As described hereinabove with reference to FIG. 1, for some applications, atrial portion 36 comprises a flange that is configured to contact the atrial side of the native valve annulus. For some applications (not shown), coronary-sinus anchor 80 is used in conjunction with an atrial portion that comprises a flange. For some applications (as shown in FIG. 8), the atrial portion comprises a plurality of atrial anchors 84, which are configured to contact the atrial side of the native valve annulus. For some such applications, the coronary-sinus anchor 80 is disposed between two of the atrial anchors as shown in FIG. 8.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with a native tricuspid valve of a heart of a mammalian subject, the native tricuspid valve including an anterior leaflet, a posterior leaflet, and a septal leaflet, and chords extending to each of the leaflets, the apparatus comprising:
- prosthetic valve leaflets;
- a valve frame, the valve frame comprising:
  - a valve-frame body that is configured to support the prosthetic valve leaflets within the native tricuspid valve, the valve-frame body comprising an atrial portion configured to be deployed in a right atrium of the subject;
  - chord-recruiting arms that are configured to extend from the valve-frame body at circumferential regions corresponding to the anterior leaflet and the posterior leaflet of the native tricuspid valve;
  - an anchoring arm that is configured to extend from the valve-frame body at a circumferential region corresponding to the septal leaflet of the native tricuspid valve, the anchoring arm being longer than each of the chord-recruiting arms; and
  - a coronary-sinus anchor that extends radially from the atrial portion of the valve-frame body, the coronary-sinus anchor being configured to be inserted into a coronary sinus of the subject and to thereby anchor the valve frame with respect to the native tricuspid valve.

2. The apparatus according to claim 1, further comprising a delivery catheter configured to:
- deliver the valve frame to the native tricuspid valve;
- deploy the chord-recruiting arms, such that the chord-recruiting arms become deployed among chords extending to each of the anterior and posterior leaflets, and the chord-recruiting arms curve around the valve-frame body circumferentially in a given circumferential direction;
- deploy the anchoring arm, such that the anchoring arm becomes deployed among chords extending to the septal leaflet, and the anchoring arm curves around the valve-frame body circumferentially in the given circumferential direction; and
- rotate at least a portion of the valve frame, in the given circumferential direction, such as:
  - to cause the chord-recruiting arms to (a) pull the anterior and posterior leaflets radially inward toward the valve frame, and (b) twist the anterior and posterior leaflets around the valve frame, by recruiting and deflecting at least a portion of the chords that extend to the anterior and posterior leaflets, and
  - to cause the anchoring arm to become anchored within the chords that extend toward the septal leaflet.

3. The apparatus according to claim 2, wherein the delivery catheter is configured to cause the valve-frame body to radially expand, such as to trap the anterior and posterior leaflets in a partially closed and twisted configuration, to thereby at least partially seal a space between the native tricuspid valve and the valve frame.

4. The apparatus according to claim 2, wherein the anchoring arm is not configured to manipulate a shape of the septal leaflet in a manner in which the chord-recruiting arms are configured to manipulate shapes of the anterior and posterior leaflets by the portion of the valve frame being rotated.

5. The apparatus according to claim 1, wherein, in a non-radially-constrained configuration of the valve frame, the chord-recruiting arms encompass less than 80 percent of a circumference of the valve-frame body.

6. The apparatus according to claim 5, wherein, in the non-radially-constrained configuration of the valve frame, the chord-recruiting arms encompass more than 40 percent of the circumference of the valve-frame body.

7. The apparatus according to claim 1, wherein the anchoring arm and the chord-recruiting arms are configured to assume chord-deployment configurations by being released from their radially constrained configurations while a portion of the valve frame from which the arms extend is still maintained in a radially-constrained configuration, and wherein the anchoring arm is configured to become deployed among chords that extend to the septal leaflet by assuming its chord-deployment configuration, and the chord-recruiting arms are configured to become deployed among chords that extend to the anterior leaflet and among chords that extend to the posterior leaflet by assuming their chord-deployment configurations.

8. The apparatus according to claim 7, wherein, in the chord-deployment configurations of the arms, a ratio of the length of the anchoring arm to lengths of each of the chord recruiting arms when measured along a center of each of the arms from a base of the arm to a tip of the arm is greater than 4:3.

9. The apparatus according to claim 8, wherein, in the chord-deployment configurations of the arms, a ratio of the length of the anchoring arm to lengths of each of the chord recruiting arms when measured along the center of each of the arms from the base of the arm to the tip of the arm is greater than 2:1.

10. An apparatus for use with a native tricuspid valve of a heart of a mammalian subject, the native tricuspid valve including an anterior leaflet, a posterior leaflet, and a septal leaflet, and chords extending to each of the leaflets, the apparatus comprising:

prosthetic valve leaflets;

a valve frame, the valve frame comprising:

a valve-frame body that is configured to support the prosthetic valve leaflets within the native tricuspid valve, the valve-frame body comprising an atrial portion configured to be deployed in a right atrium of the subject;

chord-recruiting arms that are configured to extend from the valve-frame body at circumferential regions corresponding to the anterior leaflet and the posterior leaflet of the native tricuspid valve, the valve frame not including any arms extending from the valve-frame body at a circumferential region corresponding to the septal leaflet of the native tricuspid valve; and a coronary-sinus anchor that extends radially from the atrial portion of the valve-frame body, the coronary-sinus anchor being configured to be inserted into a coronary sinus of the subject and to thereby anchor the valve frame with respect to the native tricuspid valve.

11. The apparatus according to claim 10, further comprising a delivery catheter configured to:

deliver the valve frame to the native tricuspid valve;

deploy the chord-recruiting arms, such that the chord-recruiting arms become deployed among chords extending to each of the anterior and posterior leaflets, and the chord-recruiting arms curve around the valve-frame body circumferentially in a given circumferential direction; and rotate at least a portion of the valve frame, in the given circumferential direction, such as to cause the chord-recruiting arms to (a) pull the anterior and posterior leaflets radially inward toward the valve frame, and (b) twist the anterior and posterior leaflets around the valve frame, by recruiting and deflecting at least a portion of the chords that extend to the anterior and posterior leaflets.

12. The apparatus according to claim 10, wherein, in a non-radially-constrained configuration of the valve frame, the chord-recruiting arms encompass less than 80 percent of a circumference of the valve-frame body.

13. The apparatus according to claim 12, wherein, in a non-radially-constrained configuration of the valve frame, the chord-recruiting arms encompass more than 40 percent of the circumference of the valve-frame body.

14. The apparatus according to claim 10, wherein, in a non-radially-constrained configuration of the valve frame, the valve frame does not include any chord-recruiting arms extending from the valve-frame body around at least 20 percent of a circumference of the valve-frame body.

15. The apparatus according to claim 14, wherein, in the non-radially-constrained configuration of the valve frame, the valve frame does not include any chord-recruiting arms extending from the valve-frame body around at least 30 percent of the circumference of the valve-frame body.

16. The apparatus according to claim 10, wherein the chord-recruiting arms are configured to extend from a longitudinal location along the valve-frame body and wherein, in a non-radially-constrained configuration of the valve frame, at the longitudinal location along the valve-frame body, the valve frame does not include any chord-recruiting arms around at least 20 percent of a circumference of the valve-frame body.

17. The apparatus according to claim 16, wherein, in the non-radially-constrained configuration of the valve frame, at the longitudinal location along the valve-frame body, the valve frame does not include any chord-recruiting arms around at least 30 percent of a circumference of the valve-frame body.

18. The apparatus according to claim 16, wherein the valve-frame body comprises a ventricular portion configured to be deployed in a right ventricle of the subject, and wherein the chord-recruiting arms are configured to extend from a distal end of the ventricular portion of the valve-frame body.

19. An apparatus for use with a native tricuspid valve of a heart of a mammalian subject, the native tricuspid valve including an anterior leaflet, a posterior leaflet, and a septal leaflet, and chords extending to each of the leaflets, the apparatus comprising:

prosthetic valve leaflets;

a valve frame, the valve frame comprising:

a valve-frame body that is configured to support the prosthetic valve leaflets within the native tricuspid valve, the valve-frame body comprising an atrial portion configured to be disposed in a right atrium of the subject; and a coronary-sinus anchor that extends radially from the atrial portion of the valve-frame body, the coronary-sinus anchor being configured to be inserted into a coronary sinus of the subject and to thereby anchor the valve frame with respect to the native tricuspid valve.

20. The apparatus according to claim 19, wherein the valve frame further comprises:

chord-recruiting arms that are configured to extend from the valve-frame body at circumferential regions corresponding to the anterior leaflet and the posterior leaflet of the native tricuspid valve; and an anchoring arm that is configured to extend from the valve-frame body at a circumferential region corresponding to the septal leaflet of the native tricuspid valve, the anchoring arm being longer than each of the chord-recruiting arms.

21. The apparatus according to claim 19, wherein the valve frame further comprises chord-recruiting arms that are configured to extend from the valve-frame body at circumferential regions corresponding to the anterior leaflet and the posterior leaflet of the native tricuspid valve, and the valve frame does not include any arms extending from the valve-frame body at a circumferential region corresponding to the septal leaflet of the native tricuspid valve.

* * * * *